United States Patent [19]

Hader

[11] Patent Number: 4,547,156
[45] Date of Patent: Oct. 15, 1985

[54] COUPLING FOR RELEASABLY FIXING A DENTAL PROTHESIS IN THE MOUTH

[76] Inventor: Helmut Hader, Les Allees 25, 2300 - La Chaux-De-Fonds, Switzerland

[21] Appl. No.: 580,551

[22] Filed: Feb. 14, 1984

[30] Foreign Application Priority Data

Feb. 23, 1983 [CH] Switzerland .......................... 1014/83

[51] Int. Cl.[4] .............................................. A61C 13/22
[52] U.S. Cl. ..................................... 433/172; 433/177
[58] Field of Search ................................. 433/172, 177

[56] References Cited

U.S. PATENT DOCUMENTS

| 702,857 | 6/1902 | Griswold | 433/177 |
| 866,304 | 9/1907 | Roach | 433/177 |
| 3,328,879 | 7/1967 | Bax | 437/177 |
| 4,204,321 | 5/1980 | Scott | 433/177 |
| 4,403,960 | 9/1983 | Hauri et al. | 433/177 |

FOREIGN PATENT DOCUMENTS 8203763 10/1982 PCT Int'l Appl. ................. 433/172

Primary Examiner—Robert Peshock
Attorney, Agent, or Firm—Young & Thompson

[57] ABSTRACT

The invention relates to a female part of a coupling for fixing a dental prothesis in the mouth. It comprises a casing 5 having a central void 7,8 provided with a shoulder 9. A contact piece 10 of synthetic ruby has a waisted aperture defining a fixing edge 11 of smaller diameter. This contact piece 10 is maintained against the shoulder 9 through a fixing ring 12 welded to the casing 5.

8 Claims, 3 Drawing Figures

COUPLING FOR RELEASABLY FIXING A DENTAL PROTHESIS IN THE MOUTH

The attachments or couplings for dental protheses comprise a male and a female part intended to cooperate in a press button like manner to fix a dental prothesis in the mouth. One of said parts, male or female, is fixed on the removable prothesis whereas the other is fixed in the mouth on a healthy tooth or on a pivot tooth for example.

Usually the anchoring means male and female of these couplings are made of titanium because this material is well tolerated in the mouth and of a great mechanical resistance to ensure the good working of the assembly despite the very small dimensions of these elements.

With time, the metal on metal friction of these parts causes a non negligible wear which hinders good securement of the prothesis which then wobbles.

The aim of the present invention is to provide a coupling for a dental prothesis tending to remedy this drawback and this is obtained thanks to the female part of such a coupling which is distinguished by the fact that it comprises a hard contact piece having a through hole the crossection of which is waisted, the surface of this through hole being polished or smooth.

The attached drawings show a coupling for a dental prothesis using a female part according to the invention.

Figure 1:
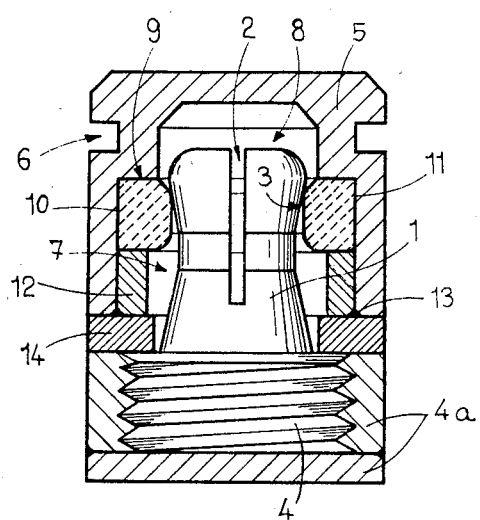
FIG. 1 shows in crossection a female part according to a first embodiment, coupled to a male part of a coupling.

The coupling for dental protheses shown in FIG. 1 comprises a male part having a stud in titanium the head of which has diametral slots 2 to give it some elasticity. The free end of the head of the stud 1 has a greater diameter than its middle portion and accordingly has a conical surface 3 intended to cooperate with a fixing edge of the female part of the coupling to lock the coupling in assembled position. This stud 1 is fastened by any known means, such as a thread 4, cooperating with a nut 4a, in a dental prothesis or in a healthy tooth for example in which the nut is fastened by overmolding or cementing.

The female part of the coupling shown comprises a housing 5 of metal, generally titanium, or any other suitable material, which has on its outside surface anchoring formation 6, for example a groove, enabling the sealing of said housing in a tooth by means of a cement or its incorporation by overmolding in a dental prothesis.

This housing 5 comprises a central aperture 7 the end 8 of which is of smaller diameter providing thus a shoulder 9.

This female part comprises further a contact piece 10 intended to cooperate with the head of the stud 2, formed by a synthetic stone, for example a ruby or a sapphire, a ceramic polished part or a of hard metal. This contact piece 10 has an outside cylindrical surface having a diameter corresponding to that of the central aperture 7 and abuts, in service position, against the shoulder 9 through one of its frontal faces. This contact piece 10 has a central through hole diverging towards the two lateral faces of said contact piece, i.e. waisted defining thus a fixing edge 11 of smaller diameter. The diameter of this fixing edge is smaller than the nominal diameter of the head of the stud 1, but the latter can, due to its resilient deformation, pass through said aperture.

Therefore in coupled position, the conical surface 3 of the stud enters of contact with the fixing edge 11 of the female part of the coupling and causes the locking of the assembly. In the example shown a washer 14 is provided so that the coupling obtained is said to be "static", i.e. without play. In a variant the washer 14 can be deleted and the stud 1 has, in coupled position, a certain play inside the female part forming thus a so-called "dynamic" coupling.

The contact piece 10 of a hard and polished material, of a hardness at least as great as that of but extremely smooth, is fixed in position in the casing by a ring 12 generally made of metal which at the example shown is laser welded in 13 onto the casing 5.

In other embodiments, this ring 12 can be screwed or driven into the casing 5.

This fixing ring has a central aperture of a diameter greater than the diameter of the aperture of the contact piece 10.

This female coupling part makes it possible, thanks to this contact piece 10, to avoid any wear of the stud 1 or of this counter piece itself and avoids thus any alteration of the quality of the coupling. This contact piece is preferably made of ruby or synthetic sapphire, i.e. corundum, but can also be made of other stone, synthetic or not. This contact piece can also be made of hard metal or ceramic. However, in this case the surface of its aperture has to be polished to a high degree to obtain the same result, i.e. the absence of wear between the contacting parts during the repeated introduction and removal of the stud 1.

In non illustrated variants of the female part of the coupling for the fixing of dental protheses, the fixing of the contact piece 10 into the casing 5 could be realized in other ways than described here above.

For example the contact piece 10 can be glued into the housing of the casing 5. Another novel way for fixing the said contact piece is to use a ring 12 of "memory" metal coming back to its original dimensions at 5° centigrade. Thus the outside diameter of said ring is provided at that temperature of 5° C., which is never reached in mouth, so that the ring is then driven in the casing 5. To put said ring in place it is cooled, causing a reduction of its outside diameter permitting its easy introduction into the housing 7, then its fixing into place is automatically obtained when the ring warms up to at least 5° C.

Figure 2:
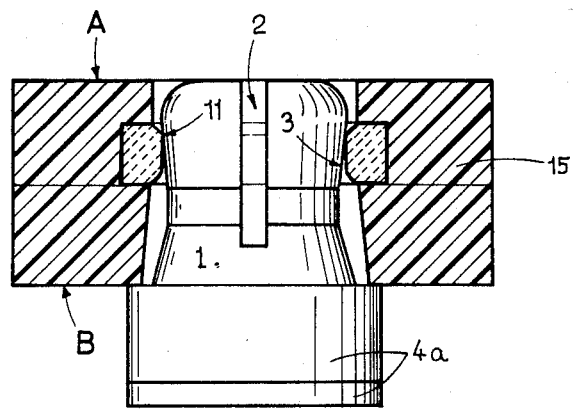
FIG. 2 shows in crossection a second embodiment of the female part coupled to a male part.

In the embodiment shown in FIG. 2, the contact piece comprised by the ring 10 can be fast by molding of a part 15 made of thermosetting synthetic resin, in lost wax or mounted and fixed mechanically in a precious or non precious dental material.

The incorporation later on of this ring 10 in a prothesis is made by overmoulding of the material forming the support of the said prothesis.

The ring 10, embedded or mechanically mounted in the part 15 is displaced with respect to the middle plan of this part so that the fixing edge 11 of the ring 10 will be located at different distances from the faces A and B of the part 15. The faces A and B can be identified for the user by means of different colours or marking signs (dynamic side and static side).

Figure 3:
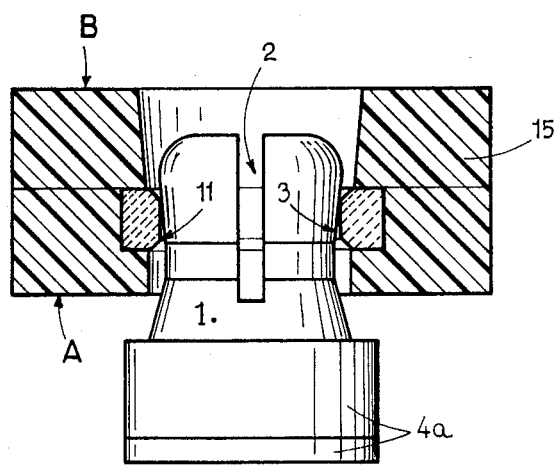
FIG. 3 shows a modified use of the female part shown in FIG. 2.

By using the female part in one direction (FIG. 2) the realized coupling is static, the stud 1 being fixed rigidly inside the female coupling part. On the other hand in the variant shown in FIG. 3, the female part being used in the opposite position, the stud is dynamically coupled i.e. with play in said female part.

What I claim is:

1. A coupling for releasably fixing a dental prosthesis in the mouth, comprising a femal epart and a male part, the female part having a rigid contact piece in hard material having a through hole that is waisted and that has a circular edge at the juncture of two annular surfaces on the contact piece that meet at said edge at an angle to each other, said annular surfaces being polished, the male part having a free end and a resiliently deformable head of a material softer than said hard material having a greatest diameter which in its undeformed condition is greater than the diameter of said edge, the male art having a portion of lesser diameter than said head on the side of said head away from said free end, said edge having line contact with said portion of lesser diameter when the male part is engaged in the female part, said line contact being the only contact between said male part and said rigid contact piece.

2. A coupling as claimed in claim 1, in which said female part is a casing having a blind recess therein to receive the male part, said casing having a shoulder thereon, said contact piece being disposed in said recess against said shoulder, and a fixing ring fastened to the housing and retaining the contact piece against said shoulder, said fixing ring having an internal diameter substantially greater than the diameter of said edge.

3. A coupling as claimed in claim 2, in which said fixing ring is of memory metal that seeks to increase its diameter at a temperature above 5° C.

4. A coupling as claimed in claim 1, in which the outer surface of the housing has anchoring formations thereon.

5. A coupling as claimed in claim 1, in which said contact piece is of corundum.

6. A coupling as claimed in claim 1, in which said contact piece is of hard metal.

7. A coupling as claimed in claim 1, in which said contact piece is of ceramic.

8. A coupling as claimed in claim 1, in which said female part is molded about said contact piece and has a hole therethrough within which said male part is received, said hole extending between opposite surfaces of said female part and said edge being disposed closer to one of said surfaces than the other of said surfaces.

* * * * *